United States Patent
Morgan et al.

(10) Patent No.: US 12,048,457 B2
(45) Date of Patent: Jul. 30, 2024

(54) COMPLIANT DEFLECTION DEVICES FOR TROCAR ASSEMBLIES

(71) Applicant: Cilag GmbH International, Zug (CH)

(72) Inventors: Jerry Morgan, Cincinnati, OH (US); Jason Harris, Mason, OH (US); Andrew Beckman, Cincinnati, OH (US); Robert Koch, Jr., Cincinnati, OH (US); Joshua Young, Cincinnati, OH (US); Kevin Houser, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 770 days.

(21) Appl. No.: 17/001,910

(22) Filed: Aug. 25, 2020

(65) Prior Publication Data

US 2020/0383701 A1 Dec. 10, 2020

Related U.S. Application Data

(62) Division of application No. 15/720,640, filed on Sep. 29, 2017, now Pat. No. 10,758,269.

(51) Int. Cl.
*A61B 17/34* (2006.01)
*A61B 17/00* (2006.01)

(52) U.S. Cl.
CPC ...... *A61B 17/3462* (2013.01); *A61B 17/3417* (2013.01); *A61B 17/3421* (2013.01); *A61B 17/3496* (2013.01); *A61B 2017/00477* (2013.01); *A61B 2017/347* (2013.01)

(58) Field of Classification Search
CPC ............ A61B 17/3462; A61B 17/3417; A61B 2017/347; A61B 17/3474; A61B 17/34; A61B 17/3421; A61B 17/3439
See application file for complete search history.

(56) References Cited

U.S. PATENT DOCUMENTS

| 6,726,699 | B1 | 4/2004 | Wright et al. |
| 9,427,255 | B2 | 8/2016 | Griffith et al. |
| 2002/0022762 | A1* | 2/2002 | Beane ............... A61B 1/127 600/101 |
| 2004/0102789 | A1 | 5/2004 | Baughman |
| 2005/0059934 | A1* | 3/2005 | Wenchell ......... A61B 18/1445 604/167.01 |

(Continued)

FOREIGN PATENT DOCUMENTS

WO 2011082114 A1 7/2011

OTHER PUBLICATIONS

Merriam-Webster Dictionary definition of Window, available at https://www.merriam-webster.com/dictionary/window, accessed Feb. 3, 2024 (Year: 2024).*

*Primary Examiner* — Amber R Stiles
(74) *Attorney, Agent, or Firm* — Vorys, Sater, Seymour and Pease LLP

(57) ABSTRACT

A trocar assembly includes a trocar housing that defines a working chamber, and a cannula having opposing proximal and distal ends and defining a lumen that extends between the proximal and distal ends. One or more windows are defined in the cannula at or near the distal end, and one or more compliant deflection devices are arranged at or near the distal end and at least partially receivable within the one or more windows. Each compliant deflection device includes a radial biasing member that extends radially inward toward a centerline of the cannula.

13 Claims, 11 Drawing Sheets

(56) References Cited

U.S. PATENT DOCUMENTS

| | | |
|---|---|---|
| 2005/0216028 A1 | 9/2005 | Hart et al. |
| 2007/0293719 A1 | 12/2007 | Scopton et al. |
| 2009/0076456 A1 | 3/2009 | Armstrong et al. |
| 2009/0105653 A1 | 4/2009 | Spenser et al. |
| 2010/0256453 A1* | 10/2010 | Hammond ......... A61B 17/3498 600/210 |
| 2011/0152773 A1* | 6/2011 | McCawley ........ A61B 17/3421 604/164.01 |
| 2012/0116313 A1 | 5/2012 | Franer et al. |
| 2014/0171739 A1* | 6/2014 | Nguyen ............... A61B 1/3132 600/114 |

* cited by examiner

COMPLIANT DEFLECTION DEVICES FOR TROCAR ASSEMBLIES

BACKGROUND

During laparoscopic surgery, one or more small incisions are formed in the skin of a patient and a trocar assembly is inserted through the incision to form a pathway that provides access to an internal body cavity, such as the patient's abdomen. The trocar assembly is used to introduce various instruments and tools into the abdomen, as well as to provide insufflation that elevates interior walls of the abdomen.

A trocar assembly generally includes a cannula, an obturator, and a housing. To set the trocar assembly for a surgical operation, the obturator is extended through an inner lumen of the cannula and is used to pierce through the patient's skin to access the abdominal cavity. To penetrate the skin, the distal end of the cannula is placed against an incision in the skin and pressure is applied to the proximal end of the trocar to force the sharp point of the obturator through the skin until it enters the targeted body cavity. The obturator can then be withdrawn, leaving the lumen of the cannula as a path to access the abdominal cavity from outside the body.

The trocar housing is attached to the proximal end of the cannula and defines a working chamber with an open distal end in communication with the lumen of the cannula. Just as the inner can receive the obturator, it is also sized to receive elongated surgical tools that are axially extended into and withdrawn from the cannula through the proximal end portion of the working chamber.

For surgical operations, a surgeon will normally use a 1:1 pairing of a trocar assembly and a surgical tool. For example, if an 8 mm (diameter) surgical tool is required for an operation, a corresponding 8 mm (diameter) trocar assembly will be used. In robotic surgery, however, trocar assemblies and surgical tools will not always enjoy a 1:1 pairing. For example, 12 mm (diameter) trocar assemblies are typically used in robotic surgery, which enables use of 12 mm (diameter) surgical tools, such as a surgical stapler. Yet some procedures require an 8 mm or 5 mm (diameter) surgical tool, which will have to pass through the 12 mm trocar assembly.

When the trocar assembly and surgical tool pairing is not 1:1, there can be "lost motion" or hysteresis to the movement where the tip (distal end) of the surgical tool is prone to various types of unintended motion, such as deflection, oscillation in place, and spring back oscillation. For instance, the initial movement input to the robot by the surgeon will not move the surgical tool, but will instead first remove the clearance between the instrument and the trocar assembly, and will subsequently move the surgical instrument. This lost motion is unacceptable to the surgeon, who expects fine control and precision from the surgical robot. The clearance between the trocar assembly and the smaller diameter surgical instrument can also result in the surgical instrument vibrating without hitting the inner walls of the trocar assembly.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to trocar assemblies and, more particularly, to compliant deflection devices used to center surgical tools within a trocar cannula of a trocar assembly and mitigate unwanted oscillation and vibration.

The embodiments described herein provide a plurality of compliant deflection devices that can be incorporated into a trocar assembly at or near the distal end of a trocar cannula. Each compliant deflection device includes a radial biasing member that extends radially inward toward a centerline of the trocar cannula. The radial biasing members help center surgical tools of varying diameters within the lumen of the cannula and minimize unintended oscillation and vibration of the surgical tools. Moreover, the radial biasing members may also be flexible or pliant so that they are able to accommodate larger diameter surgical tools without unduly obstructing operation of the larger diameter surgical tools.

Figure 1:
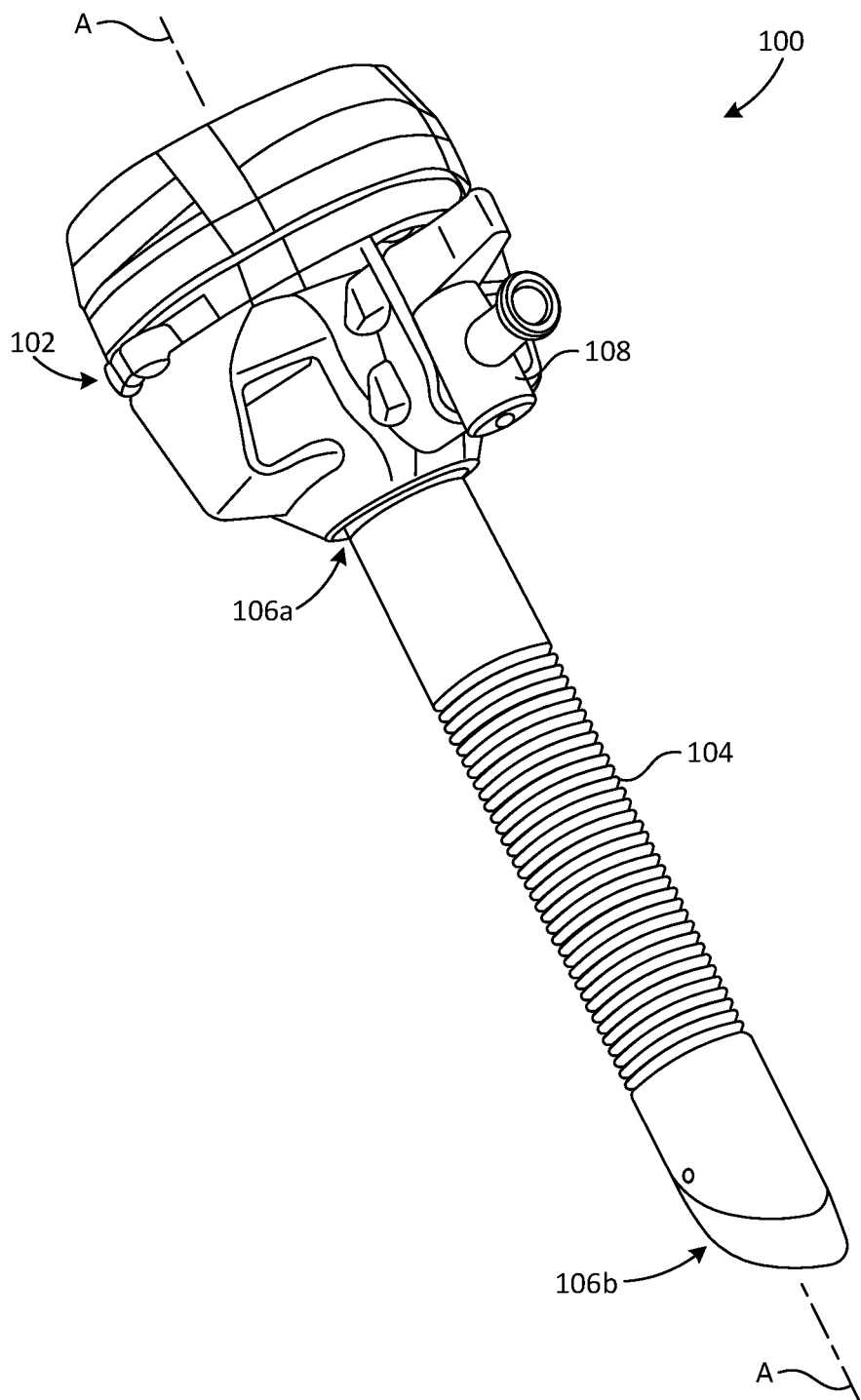
FIG. 1 is an isometric view of an example trocar assembly that may incorporate the principles of the present disclosure.

FIG. 1 is an isometric view of an example trocar assembly 100 that may incorporate the principles of the present disclosure. The depicted trocar assembly 100 is just one example trocar assembly that can suitably incorporate the principles of the present disclosure. Indeed, many alternative designs and configurations of the trocar assembly 100 may be employed, without departing from the scope of this disclosure. For example, another suitable trocar assembly that may suitably incorporate the principles of the present disclosure is described in co-owned U.S. Pat. No. 7,918,826 entitled "Trocar Assembly".

As illustrated, the trocar assembly 100 includes a trocar housing 102 and a cannula 104 that has a proximal end 106a and a distal end 106b. The cannula 104 is coupled to the trocar housing 102 at the proximal end 106a and extends distally therefrom. In some embodiments, the cannula 104 may comprise an integral extension of the trocar housing 102. In other embodiments, however, the trocar housing 102 and the cannula 104 may comprise two separate components that can be mated to one another.

The trocar assembly 100 may also include an insufflation valve 108 (e.g., a stopcock valve) coupled to the trocar housing 102 or forming an integral part thereof. The insufflation valve 108 is operable to introduce an insufflation fluid (e.g. carbon dioxide) into the trocar housing 102 and the cannula 104 and subsequently into an inner cavity (e.g., the abdomen) of a patient to elevate the interior walls of the inner cavity. While not shown, the trocar assembly 100 may also include an obturator extendable through the trocar assembly along a centerline A of the trocar assembly 100. When used, the obturator extends through the cannula 104 and out the distal end 106b to penetrate a patient's skin and thereby facilitate access to the abdominal cavity.

Figure 2:
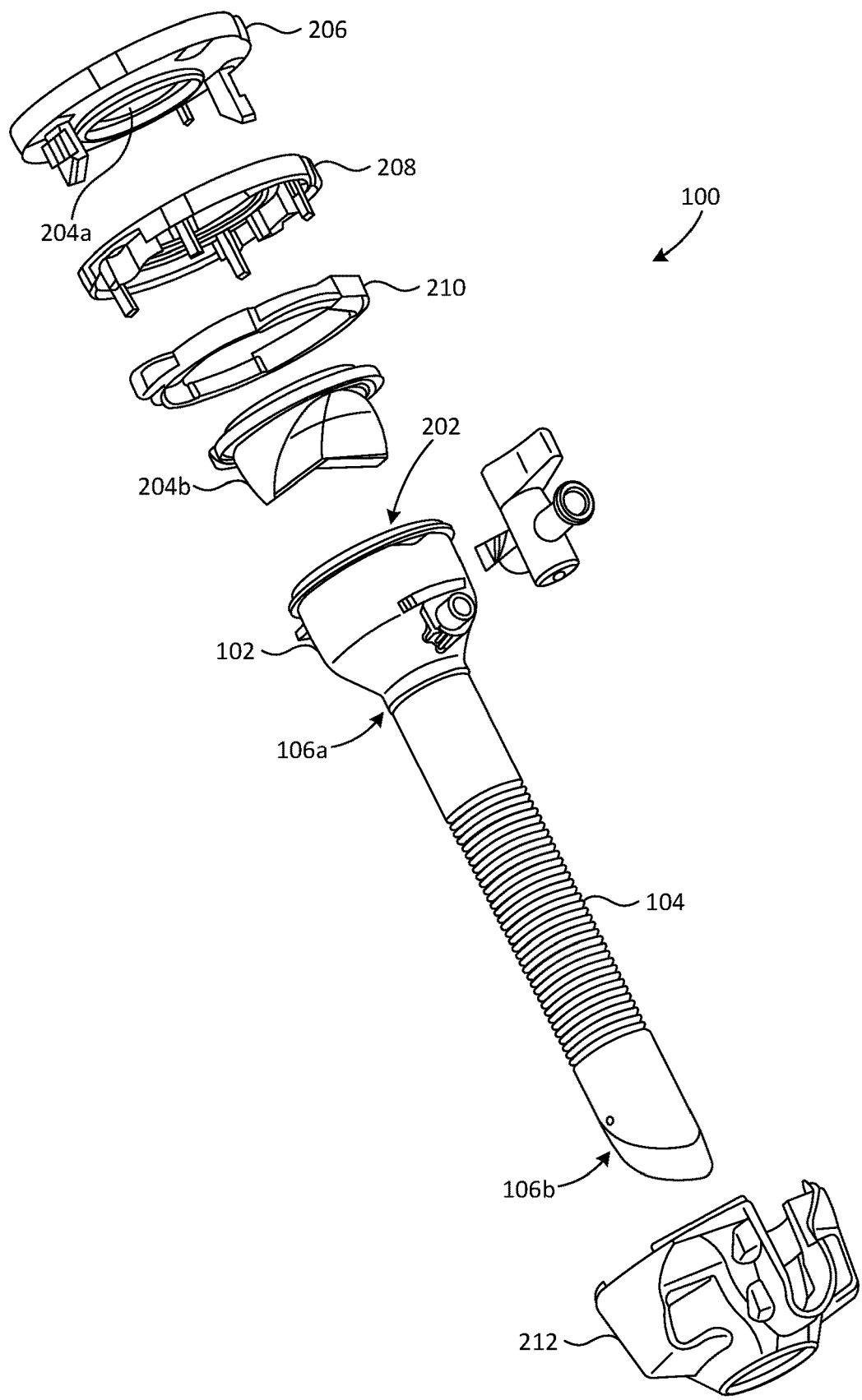
FIG. 2 is an exploded view of the trocar assembly of FIG. 1.

FIG. 2 is an exploded view of the trocar assembly 100 of FIG. 1. The trocar housing 102 provides and otherwise defines a working chamber 202 that communicates with an inner lumen defined within the cannula 104. The lumen is open-ended and extends between the proximal and distal ends 106a,b of the cannula 104.

The working chamber 202 is also open-ended and configured to at least partially receive a first or "proximal" seal assembly 204a and a second or "distal" seal assembly 204b. The first and second seal assemblies 204a,b allow selective sealing of the working chamber 202 during operation. In at least one embodiment, as illustrated, the second seal assembly 204b may comprise a duckbill seal. While two seal assemblies 204a,b are depicted in FIG. 2, the trocar assembly 100 may alternatively include more or less than two seal assemblies, without departing from the scope of the disclosure.

The first and second seal assemblies 204a,b may be secured (at least partially) within the working chamber 202 via a variety of ways. In the illustrated embodiment, for example, a crown ring 206 and a gasket ring 208 may be snap-fit together, and a gasket retainer ring 210 may be configured to secure an attachment between the gasket ring 208 and the trocar housing 102. A housing retainer 212 may then be extended about the exterior of the trocar housing 102 to secure the internal components to the trocar housing 102.

Figure 3:
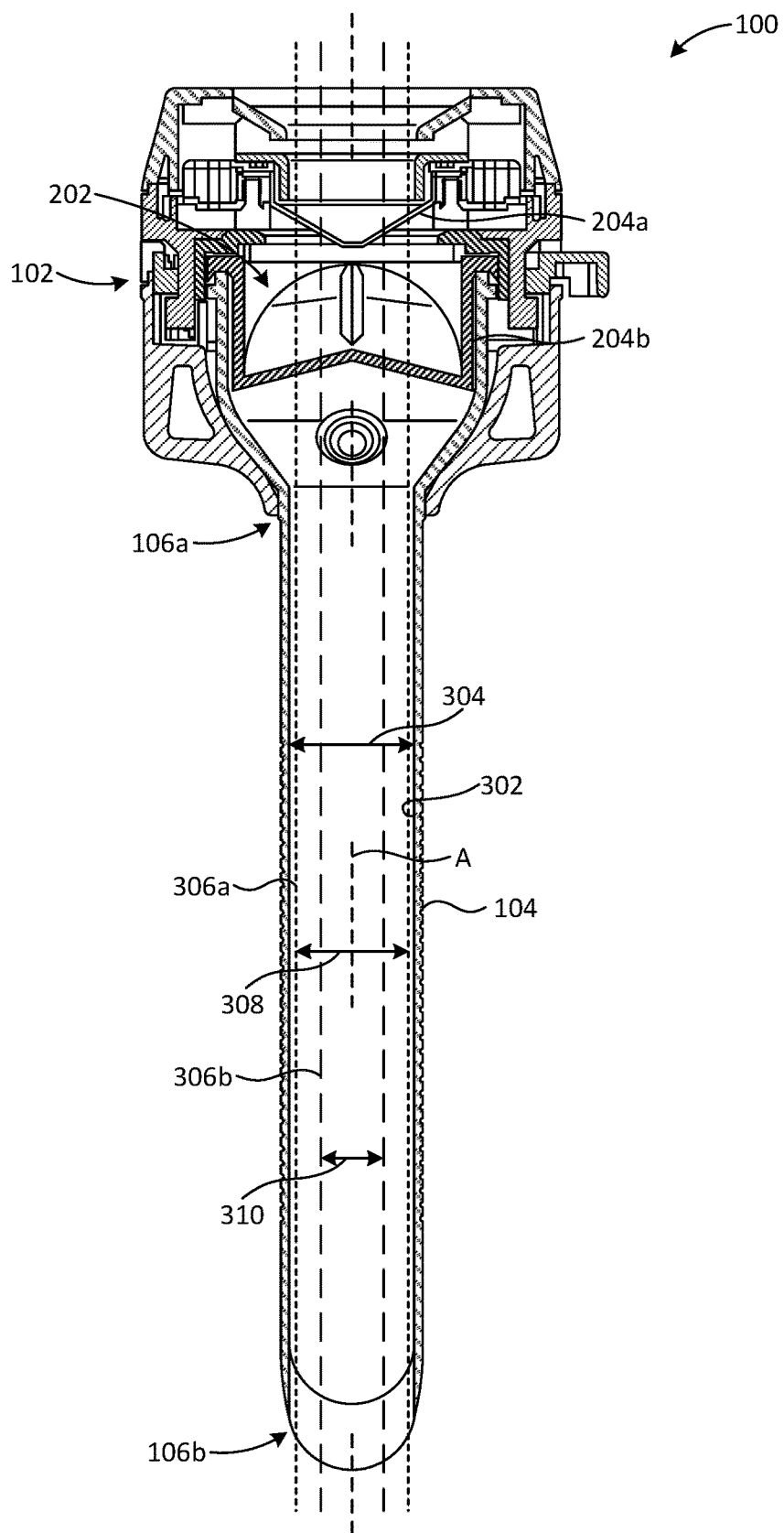
FIG. 3 is a cross-sectional side view of the trocar assembly of FIG. 1.

FIG. 3 is a cross-sectional side view of the trocar assembly 100. As illustrated, the cannula 104 defines and otherwise provides a lumen 302 that extends between the proximal and distal ends 106a,b and communicates with the working chamber 202 provided by the trocar housing 102. The lumen 302 exhibits an inner diameter 304 configured to receive surgical tools having an outer diameter equal to (i.e., slightly less than equal) or less than the inner diameter 304.

In at least one embodiment, the inner diameter 304 may be sized to receive a 12 mm surgical tool. In such embodiments, the trocar assembly 100 may be referred to and otherwise characterized as a "12 mm trocar," which is commonly used in robotic surgery to accommodate various 12 mm surgical tools, such as surgical staplers. In the illustrated embodiment, a first surgical tool 306a is depicted in dashed lines as extended through the trocar assembly 100 and projecting out each end. While not explicitly shown, as the first surgical tool 306a is extended into the trocar assembly 100, the first and second seal assemblies 204a,b are configured to deform and provide a sealed interface against the outer surface of the first surgical tool 306a.

The first surgical tool 306a exhibits an outer diameter 308 of approximately 12 mm, which is slightly smaller than the inner diameter 304 of the lumen 302. Accordingly, the first surgical tool 306a may be referred to as a "12 mm surgical tool" and the lumen 302 is sized to receive the first surgical tool 306a such that very little space (e.g., less than 1 mm) remains between the inner and outer diameters 304, 308. Consequently, the first surgical tool 306a is generally centered within the cannula 302 along the centerline A at all times, which tends to mitigate unwanted occurrences of deflection, oscillation, and vibration of the first surgical tool 306a.

At times, however, smaller surgical tools may need to be introduced into the trocar assembly 100 to perform additional procedures. In the illustrated embodiment, for example, a second surgical tool 306b is depicted in dashed lines as extended through the trocar assembly 100 and projecting out each end. Similar to the first surgical tool 306a, and while not explicitly shown, as the second surgical tool 306b is extended into the trocar assembly 100, the first and second seal assemblies 204a,b are configured to deform and provide a sealed interface against the outer surface of the second surgical tool 306b.

The second surgical tool 306b exhibits an outer diameter 310 that is smaller than the outer diameter 308 of the first surgical tool 306a, and smaller than the inner diameter 304 of the lumen 302. In some applications, for example, the outer diameter 310 may be approximately 8 mm. In such applications, the second surgical tool 306b may be referred to as an "8 mm surgical tool." Alternatively, the outer diameter 310 may be approximately 5 mm, and the second surgical tool 306b may instead be referred to as a "5 mm surgical tool."

Since the outer diameter 310 of the second surgical tool 306b is much smaller than the inner diameter 304 of the lumen 302, the second surgical tool 306b will rarely (if ever) be centered within the cannula 302 along the centerline A during operation. Rather, during operation the second surgical tool 306b will continuously be prone to deflection, oscillation in place, spring back oscillation, and vibration as the second surgical tool 306b is manipulated in various directions. As discussed above, such unintended "lost motion" or hysteresis is unacceptable to a surgeon, who expects fine control and precision from during robotic operations.

According to embodiments of the present disclosure, the trocar assembly 100 may incorporate a plurality of compliant deflection devices arranged at or near the distal end 106b of the cannula 104. Each compliant deflection device includes at least one radial biasing member that extends radially inward to engage the outer surface of surgical tools extended within the cannula 104. The radial biasing members may be flexible or pliable and thereby capable of accommodating varying diameters of surgical tools that may be used in the trocar assembly 100. The radial biasing members may help center the surgical tools within the cannula and eliminate or significantly minimize unintended oscillation and vibration. Because of their flexibility, the radial biasing members will not obstruct (inhibit) larger-diameter surgical tools (e.g., the first surgical tool 306a) but are instead able to accommodate its larger-diameter features.

Figure 4A:
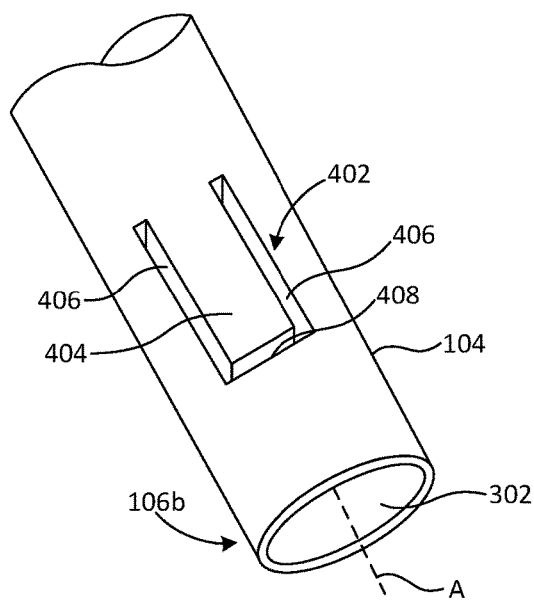
FIG. 4A is an isometric side view of the distal end of a trocar cannula and showing an example compliant deflection device that may be incorporated into the trocar assembly of FIGS. 1-3.

FIG. 4A is an isometric side view of the cannula 104 showing an example compliant deflection device 402 that may be incorporated into the trocar assembly 100 of FIGS. 1-3, according to one or more embodiments of the present disclosure. As illustrated, the compliant deflection device 402 may be positioned and otherwise arranged at or near the distal end 106b of the cannula 104. While only one compliant deflection device 402 is depicted in FIG. 4A, a plurality of compliant deflection devices 402 (i.e., at least two) may be included at or near the distal end 106b. In some embodiments, the compliant deflection devices 402 may be equidistantly spaced from each other about the circumference of the cannula 104, but could alternatively be spaced in any desired configuration. Embodiments with two compliant deflection devices 402, for example, may be angularly offset from each other by approximately 180°, embodiments with three compliant deflection devices 402 may be angularly offset from each other by approximately 120°, and embodiments with four compliant deflection devices 402 may be angularly offset from each other by approximately 90°.

The compliant deflection device 402 includes a radial biasing member 404 that extends radially inward toward the centerline A of the cannula 104. In the illustrated embodiment, the radial biasing member 404 is in the form of a tab or longitudinal extension defined in the wall of the cannula 104. The radial biasing member 404 may be formed by making two longitudinal cuts 406 connected by a transverse cut 408. Each cut 406, 408 extends entirely through the wall of the cannula 104 between the inner and outer surfaces thereof. The longitudinal cuts 406 extend longitudinally and substantially parallel to the centerline A, and the transverse cut 408 extends circumferentially and substantially orthogonal to the centerline A.

The radial biasing member 404 may be flexible to provide a radially inward biasing force when acted upon by a surgical tool present within the lumen 302. Once the surgical tool is removed, the radial biasing member 404 may naturally and elastically return to its relaxed state. To provide the required flexibility, the radial biasing member 404 may be made of a resilient material. In some embodiments, the radial biasing member 404 will be made of the same material used to manufacture the cannula 104. In such embodiments, the resilient material may include, but is not limited to, stainless steel, spring steel, plastic, and nylon. In other embodiments, the radial biasing member 404 may be made of a material that is dissimilar to that of the cannula 104. In such embodiments, the resilient material may include, but is not limited to, vinyl, polyurethane, polyethylene, polypropylene, rubber (e.g., natural rubber, synthetic rubber, nitrile rubber, silicone rubber, a urethane rubber, a polyether rubber, chloroprene rubber, ethylene propylene diene monomer, styrene-butadiene rubber, etc.), silicone, or any combination thereof.

Figures 4B, 4C, 4D, 4E:
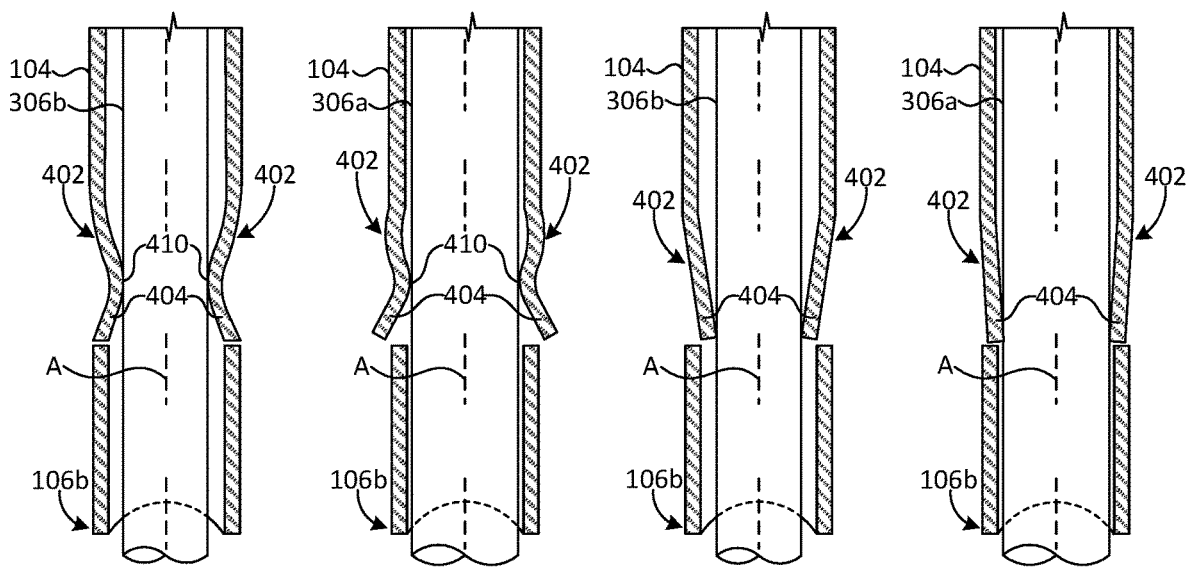
FIGS. 4B and 4C are cross-sectional side views of the distal end of the cannula of FIG. 4A and show example operation of two example compliant deflection devices.
FIGS. 4D and 4E are cross-sectional side views of the distal end of the cannula of FIG. 4A and show example operation of two additional example compliant deflection devices.

FIGS. 4B and 4C are cross-sectional side views of the distal end 106b of the cannula 104 and show two example compliant deflection devices 402 in example operation, according to one or more embodiments. As illustrated, the two compliant deflection devices 402 are provided on angularly opposite sides of the cannula 104 and arranged at or near the distal end 106b thereof. Moreover, the radial biasing member 404 of each compliant deflection device 402 is formed or otherwise bent to provide a concave portion 410 that protrudes radially inward toward the centerline A of the cannula 104.

The compliant deflection devices 402 may be movable between a relaxed position, as shown in FIG. 4B, and a biased position, as shown in FIG. 4C. In FIG. 4B, the second surgical tool 306b is extended through the cannula 104 and out the distal end 106b. The radial biasing members 404 protrude radially inward and may or may not engage the outer radial surface of the second surgical tool 306b. The radial biasing members 404 operate to generally center the second surgical tool 306b within the lumen 302, and thereby eliminate or significantly minimize unintended oscillation and/or vibration of the second surgical tool 306b.

FIG. 4C shows the larger-diameter first surgical tool 306a extended into the cannula 104, which urges (moves) the compliant deflection devices 402 to the biased position. More specifically, the radial biasing members 404 engage the outer surface of the first surgical tool 306a and are forced radially outward to accommodate the larger outer diameter. Since the radial biasing members 404 are made of a resilient (flexible) material, once the first surgical tool 306a is removed from the cannula 104, the radial biasing members 404 will naturally return to the relaxed position. Accordingly, the compliant deflection devices 402 are able to radially expand and conform to the outer diameter of the first surgical tool 306a and thereby eliminate or significantly minimize unintended oscillation and/or vibration of the first surgical tool 306a.

FIGS. 4D and 4E are cross-sectional side views of another embodiment of two compliant deflection devices 402 during example operation. Similar to the embodiment of FIGS. 4B and 4C, the two compliant deflection devices 402 in FIGS. 4D and 4E are provided on angularly opposite sides of the cannula 104 and are arranged at or near the distal end 106b thereof. Unlike the radial biasing members 404 in FIGS. 4B and 4C, however, the radial biasing members 404 in FIGS. 4D and 4E are each simply bent radially inward toward the centerline A of the cannula 104.

The compliant deflection devices 402 are again movable between a relaxed position, as shown in FIG. 4D, and a biased position, as shown in FIG. 4E. In FIG. 4D, the radial biasing members 404 angle radially inward and potentially engage the outer radial surface of the second surgical tool 306b. The radial biasing members 404 help center the second surgical tool 306b within the lumen 302 and help eliminate or significantly minimize unintended oscillation and/or vibration of the second surgical tool 306b.

FIG. 4D shows the larger-diameter first surgical tool 306a extended through the cannula 104, which forces the radial biasing members 404 radially outward to the biased position. Since the radial biasing members 404 are made of a resilient material, removing the first surgical tool 306a from the cannula 104 allows the radial biasing members 404 to naturally return to the relaxed position. Accordingly, the compliant deflection devices 402 compliantly expand to conform to the outer diameter of the first surgical tool 306a and also eliminate or significantly minimize unintended oscillation and/or vibration of the first surgical tool 306a.

In some embodiments, the radial biasing members 404 may be lubricious (e.g., slippery or slick), which may advantageously reduce the drag force against any surgical tool passing through the cannula 104. In some embodiments, for example, the resilient material of the radial biasing members 404 may comprise a lubricious material. In other embodiments, however, the radial biasing members 404 may be coated with a lubricious substance or material such as, but not limited to, oil, graphite, TEFLON™, silicone, and any combination thereof.

Figure 5A:
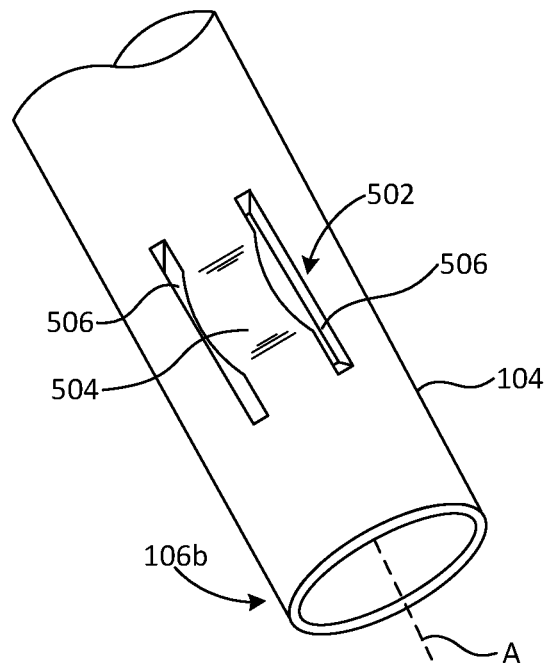
FIG. 5A is an isometric side view of the distal end of a trocar cannula and showing another example compliant deflection device that may be incorporated into the trocar assembly of FIGS. 1-3.

FIG. 5A is an isometric side view of the cannula 104 and showing another example compliant deflection device 502 that may be incorporated into the trocar assembly 100 of FIGS. 1-3, according to one or more embodiments of the present disclosure. Similar to the compliant deflection device 402 of FIG. 4A, the compliant deflection device 502 may be arranged at or near the distal end 106b of the cannula 104. Moreover, while only one compliant deflection device 502 is depicted in FIG. 5A, a plurality (i.e., at least two) of compliant deflection devices 502 may be included at or near the distal end 106b and spaced equidistantly or non-equidistantly from each other about the circumference of the cannula 104.

The compliant deflection device 502 includes a radial biasing member 504 that extends radially inward toward the centerline A of the cannula 104. In the illustrated embodiment, the radial biasing member 504 is in the form of a longitudinal extension defined in the wall of the cannula 104 by making two longitudinal cuts 504 that extend entirely through the wall of the cannula 104 between the inner and outer surfaces thereof. The longitudinal cuts 504 extend substantially parallel to the centerline A.

The radial biasing member 504 includes and otherwise defines a radial projection that protrudes radially inward relative to the outer wall of the cannula 104 and toward the centerline A of the cannula 104. Moreover, the radial biasing member 504 may be made of any of the resilient materials mentioned herein. Accordingly, the radial biasing member 504 provides a radially inward biasing force when acted upon by a surgical tool extended within the cannula 104, and once the surgical tool is removed, the radial biasing member 504 will naturally and elastically return to its relaxed state.

Figures 5B, 5C:
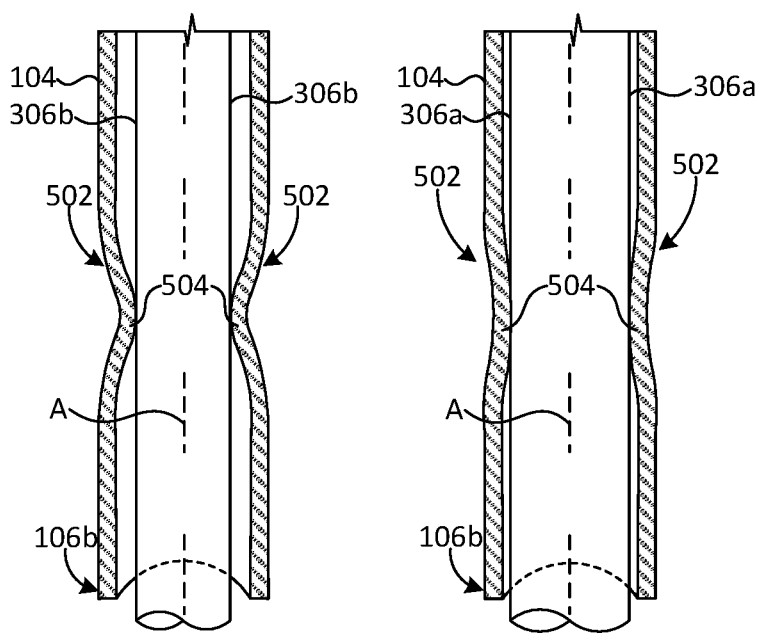
FIGS. 5B and 5C are cross-sectional side views of the distal end of the cannula of FIG. 5A and show example operation of two additional example compliant deflection devices.

FIGS. 5B and 5C are cross-sectional side views of the distal end 106b of the cannula 104 and show example operation of two compliant deflection devices 502, according to one or more embodiments. As illustrated, the two compliant deflection devices 502 are provided on angularly opposite sides of the cannula 104. Moreover, the compliant deflection devices 502 may be movable between a relaxed position, as shown in FIG. 5B, and a biased position, as shown in FIG. 5C. In FIG. 5B, the second surgical tool 306b is extended through the cannula 104 and the radial biasing members 504 potentially engage the outer radial surface of the second surgical tool 306b as protruding radially inward. Accordingly, the radial biasing members 504 help center the second surgical tool 306b within the cannula 104 and eliminate or significantly minimize unintended oscillation and/or vibration of the second surgical tool 306b.

FIG. 5C shows the larger-diameter first surgical tool 306a extended into the cannula 104, which moves the compliant deflection devices 502 to the biased position. As the first surgical tool 306a enters the cannula 104, the radial biasing members 504 are forced radially outward to accommodate the larger outer diameter. Since the radial biasing members 504 are made of a resilient material, removing the first surgical tool 306a from the cannula 104 allows the radial biasing members 504 to naturally return to the relaxed position. Accordingly, the radial biasing members 504 compliantly expand and conform to the outer diameter of the first surgical tool 306a and thereby eliminate or significantly minimize unintended oscillation and/or vibration of the first surgical tool 306a.

Similar to the radial biasing members 404 of FIGS. 4A-4E, the radial biasing members 504 may be made of or coated with a lubricious substance or material, which reduces the drag force of any surgical tool passing through the cannula 104.

Figure 6A:
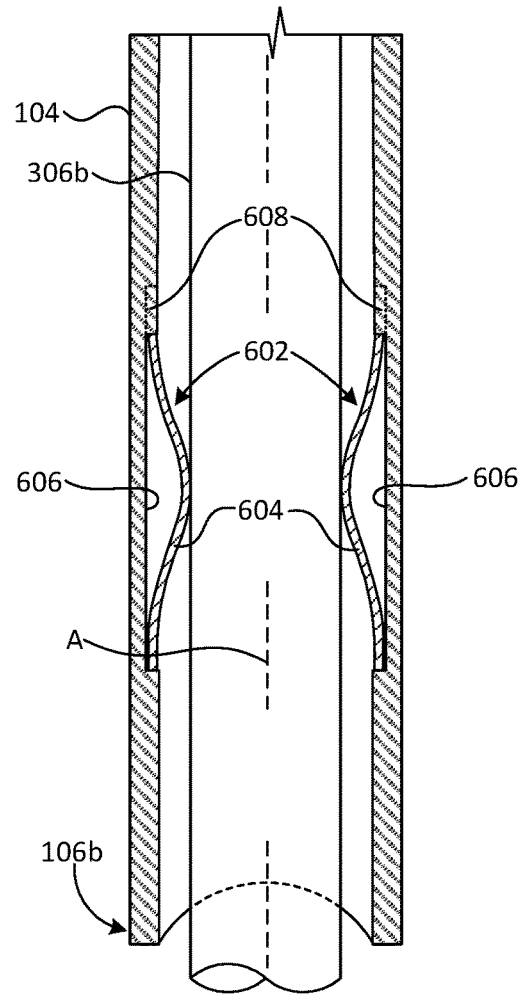
FIGS. 6A and 6B are cross-sectional side views of the distal end of the trocar cannula of FIGS. 1-3 and show example operation of two additional example compliant deflection devices.
Figure 6B:
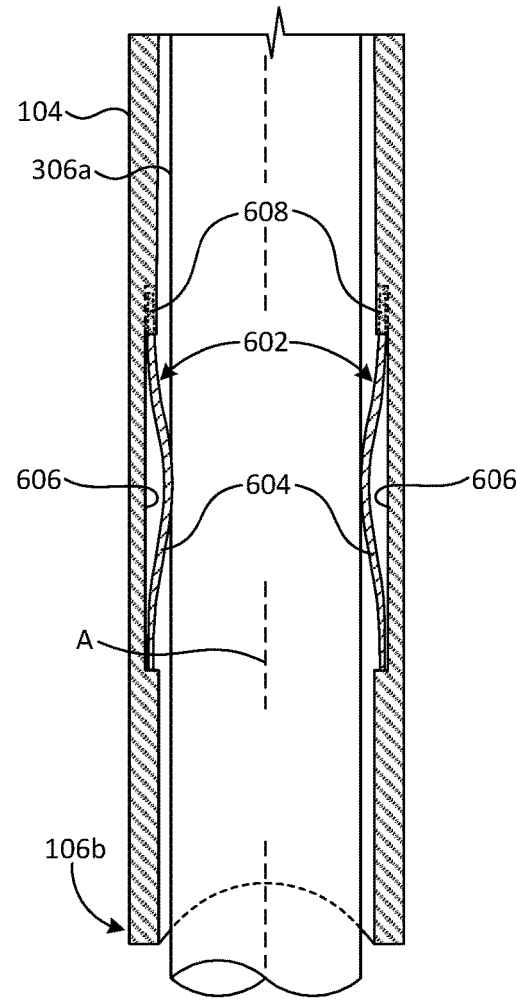

FIGS. 6A and 6B are cross-sectional side views of the distal end 106b of the cannula 104 of FIGS. 1-3 and show example operation of two additional compliant deflection devices 602, according to one or more embodiments. As illustrated, the two compliant deflection devices 602 are arranged within the cannula 104 and provided on angularly opposite sides of the cannula 104. Moreover, while only two compliant deflection devices 602 are depicted in FIGS. 6A and 6B, more than two compliant deflection devices 602 may be employed and they may be equidistantly or non-equidistantly spaced from each other about the circumference of the cannula 104.

The compliant deflection devices 602 each include a radial biasing member 604 that protrudes (extends) radially inward toward the centerline A of the cannula 104. In the illustrated embodiment, the radial biasing members 604 are in the form of bow springs arranged within a corresponding groove 606 defined on the inner radial surface of the cannula 104. The radial biasing members 604 may be made of any of the resilient materials mentioned herein. In operation, each radial biasing member 604 provides a radially inward biasing force when acted upon by a surgical tool extended within the cannula 104, and once the surgical tool is removed, the radial biasing members 604 may naturally and elastically return to their relaxed state.

The compliant deflection devices 602 (e.g., the radial biasing members 604) may be movable between a relaxed position, as shown in FIG. 6A, and a biased position, as shown in FIG. 6B. In FIG. 6A, the second surgical tool 306b is extended through the cannula 104 and the radial biasing members 604 protrude radially inward to potentially engage the outer radial surface of the second surgical tool 306b. The radial biasing members 604 help center the second surgical tool 306b within the lumen 302 and also eliminate or significantly minimize unintended oscillation and/or vibration of the second surgical tool 306b.

FIG. 6B shows the larger-diameter first surgical tool 306a extended within the cannula 104, which moves the compliant deflection devices 602 to the biased position. As the first surgical tool 306a extends through the cannula 104, the radial biasing members 604 engage the outer radial surface of the first surgical tool 306a and are forced (compressed) radially outward to accommodate the larger-diameter tool. In addition, as the radial biasing members 604 are radially compressed, the axial length of each radial biasing member 604 increases in the proximal and distal directions. In one or more embodiments, at least one end of each radial biasing member 604 may be extendable within a pocket 608 (shown in dashed lines) defined in the inner radial surface of the cannula 104. The pocket 608 provides an area to receive an axial end of the radial biasing member 604, thereby allowing the radial biasing member 604 to axially extend without obstruction.

Since the radial biasing members 604 are made of a resilient material, removing the first surgical tool 306a from the cannula 104 allows the radial biasing members 604 to naturally return to their relaxed state. Accordingly, the compliant deflection devices 602 compliantly expand and conform to the outer diameter of the first surgical tool 306a and thereby eliminate or significantly minimize unintended oscillation and/or vibration of the first surgical tool 306a. Moreover, in at least one embodiment, the radial biasing members 604 may be made of or coated with a lubricious substance or material, which reduces the drag force of any surgical tool passing therethrough.

Figure 7A:
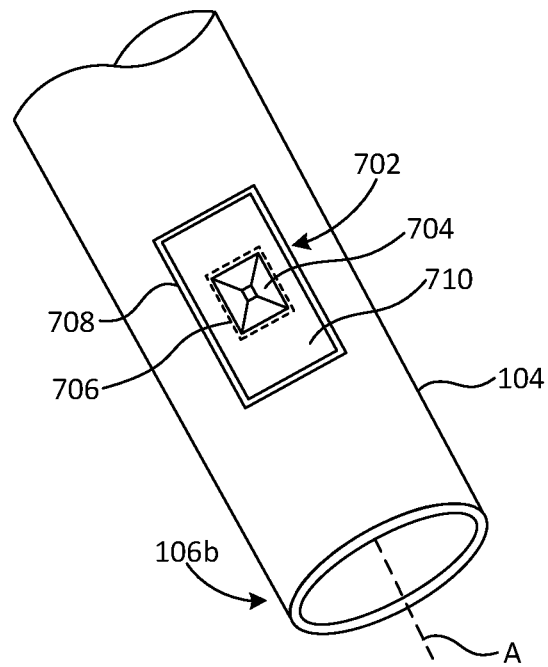
FIG. 7A is an isometric side view of a trocar cannula and shows another example compliant deflection device that may be incorporated into the trocar assembly of FIGS. 1-3.

FIG. 7A is an isometric side view of the cannula 104 and shows another example compliant deflection device 702 that may be incorporated into the trocar assembly 100 of FIGS. 1-3, according to one or more embodiments of the present disclosure. As with prior embodiments, the compliant deflection device 702 may be arranged at or near the distal end 106b of the cannula 104. Moreover, while only one compliant deflection device 702 is depicted in FIG. 7A, a plurality (i.e., at least two) of compliant deflection devices 702 may be included at or near the distal end 106b and spaced equidistantly or non-equidistantly from each other about the circumference of the cannula 104.

The compliant deflection device 702 may be arranged on the exterior or outer surface of the cannula 104. Moreover, the compliant deflection device 702 includes a radial biasing member 704 that extends through a window 706 (shown in dashed lines) defined through the wall of the cannula 104 and radially inward toward the centerline A of the cannula 104.

In the illustrated embodiment, a depression 708 (e.g., a pocket or cavity) is defined on the outer radial surface of the cannula 104 and is configured to receive the compliant deflection device 702 in a flush mounted configuration. The compliant deflection device 702 includes a body 710 sized to be received into the depression 708. While the depression 708 and the body 710 are depicted as rectangular, and the radial biasing member 704 and the window 706 are depicted as square, it will be appreciated that other shapes may be employed for any of these components, such as circular or other polygonal shapes, without departing from the scope of the disclosure.

The compliant deflection device 702, and at least the radial biasing member 704, may be made of any of the resilient materials mentioned herein. In at least one embodiment, the radial biasing member 704 is made of an elastomer, rubber, or silicone. In operation, the radial biasing member 704 provides a radially inward biasing force when acted upon by a surgical tool extended within the cannula 104. Once the surgical tool is removed from the cannula 104, the radial biasing member 704 will naturally and elastically return to its relaxed state.

Figure 7B:
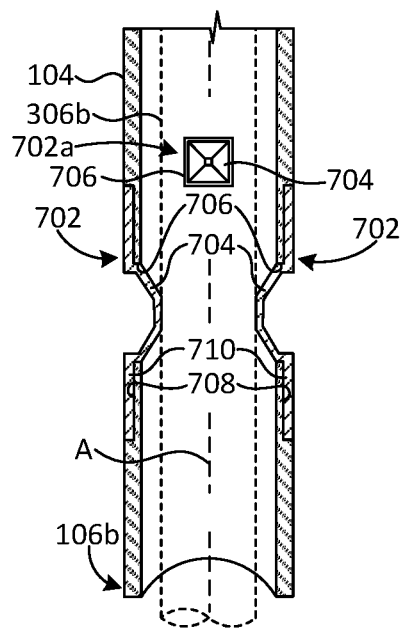
FIGS. 7B and 7C are cross-sectional side views of the distal end of the cannula of FIG. 7A and show example operation of two additional example compliant deflection devices.
Figure 7C:
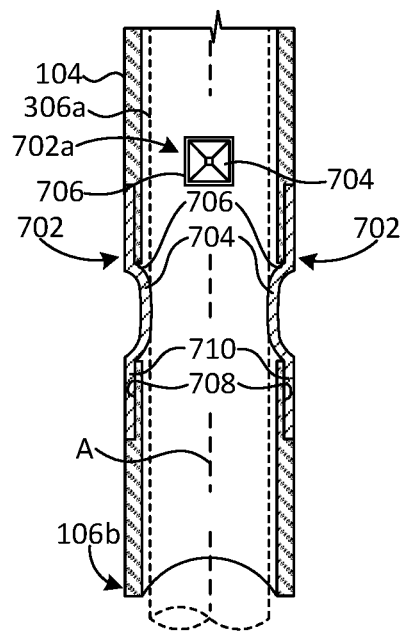

FIGS. 7B and 7C are cross-sectional side views of the distal end 106b of the cannula 104 and show example operation of two compliant deflection devices 702, according to one or more embodiments. As illustrated, the two compliant deflection devices 702 are provided on angularly opposite sides of the cannula 104. Also illustrated is a third compliant deflection device 702a angularly offset from the two compliant deflection devices 702 by approximately 90°. The third compliant deflection device 702a is axially offset from the other compliant deflection devices 702, but could alternatively be aligned axially, without departing from the scope of the disclosure.

The body 710 of each compliant deflection device 702 is received within a corresponding depression 708 defined in the outer radial surface of the cannula 104. The body 710 may be secured within its corresponding depression 708 via a variety of attachment means including, but not limited to, one or more mechanical fasteners, welding, brazing, an adhesive, an interference fit, a shrink fit, or any combination thereof. In at least one embodiment, the compliant deflection devices 702 may be over molded onto the cannula 104 and thereby secured within the corresponding depression 708. In other embodiments, however, the radial biasing member 704 may be sized to be received within its corresponding window 706 via an interference or shrink fit, and thereby secure the compliant deflection devices 702, 702a to the cannula 104.

In the illustrated embodiment, the radial biasing members 704 are in the form of collapsible protrusions or projections. The radial biasing members 704 may be movable (transitionable) between a relaxed position, as shown in FIG. 7B, and a biased position, as shown in FIG. 7C. In FIG. 7B, the second surgical tool 306b (shown in dashed lines) is extended through the cannula 104 and the radial biasing members 704 potentially engage the outer radial surface of the second surgical tool 306b to help center the second surgical tool 306b within the cannula 104 and eliminate or significantly minimize unintended oscillation and/or vibration.

FIG. 7C shows the larger-diameter first surgical tool 306a extended into the cannula 104, which forces the radial biasing members 704 to at least partially collapse and otherwise move radially outward (i.e., away from the centerline A) to accommodate the larger outer diameter. Since the radial biasing members 704 are made of a resilient (flexible) material, removing the first surgical tool 306a from the cannula 104 allows the radial biasing members 704 to naturally return (expand or re-inflate) to the relaxed position. Accordingly, the radial biasing members 704 conform to the outer diameter of the first surgical tool 306a and thereby eliminate or significantly minimize unintended oscillation and/or vibration of the first surgical tool 306a.

In one or more embodiments, the radial biasing members 704 may be made of or coated with a lubricious substance or material, which reduces the drag force of any surgical tool passing therethrough.

Figure 8A:
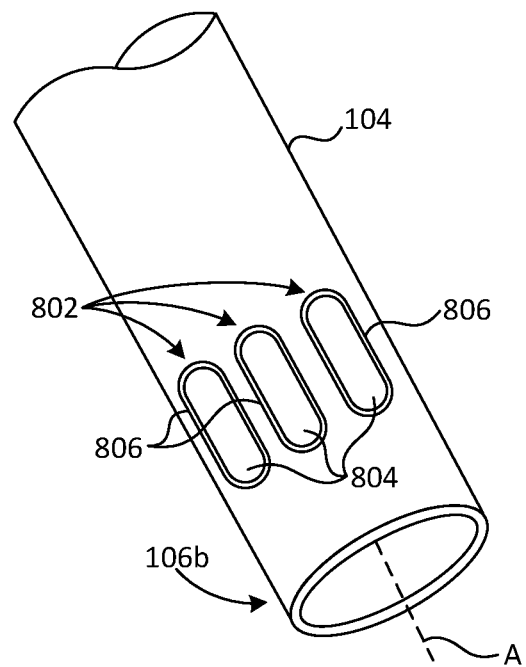
FIG. 8A is an isometric side view of a trocar cannula and shows another example of a plurality of compliant deflection devices that may be incorporated into the trocar assembly of FIGS. 1-3.

FIG. 8A is an isometric side view of the cannula 104 and shows another example of a plurality of compliant deflection devices 802 that may be incorporated into the trocar assembly 100 of FIGS. 1-3, according to one or more embodiments of the present disclosure. As with prior embodiments, the compliant deflection devices 802 may be arranged at or near the distal end 106b of the cannula 104. Moreover, while three compliant deflection devices 802 are depicted in FIG. 8A, at least two compliant deflection devices 802 may be included at or near the distal end 106b and spaced equidistantly or non-equidistantly from each other about the circumference of the cannula 104.

In the illustrated embodiment, each compliant deflection device 802 includes a radial biasing member 804 in the form of an insert seated within a corresponding window 806 defined through the wall of the cannula 104. While the radial biasing member 804 and the windows 806 are depicted as generally oval structures, other shapes (e.g., polygonal) may be employed, without departing from the scope of the disclosure. The radial biasing members 804 may be made of any of the resilient materials mentioned herein. In at least one embodiment, the radial biasing members 804 are made of rubber or silicone.

Each radial biasing member 804 protrudes radially inward through the corresponding window 806 and toward the centerline A. The radial biasing members 804 operate to provide a radially inward biasing force upon contacting the outer surface of surgical tools extended within the cannula 104. In some embodiments, the radial biasing members 804 may be urged (forced) out the corresponding window 806 and away from the centerline A when acted upon by larger-diameter surgical tools within the cannula 104. Once the surgical tool is removed, however, the radial biasing members 804 may naturally or elastically return to their relaxed state.

Figure 8B:
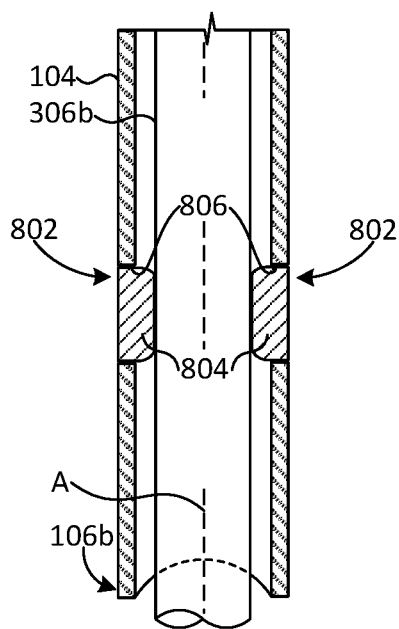
FIGS. 8B and 8C are cross-sectional side views of the distal end of the cannula of FIG. 8A and show example operation of two example compliant deflection devices.
Figure 8C:
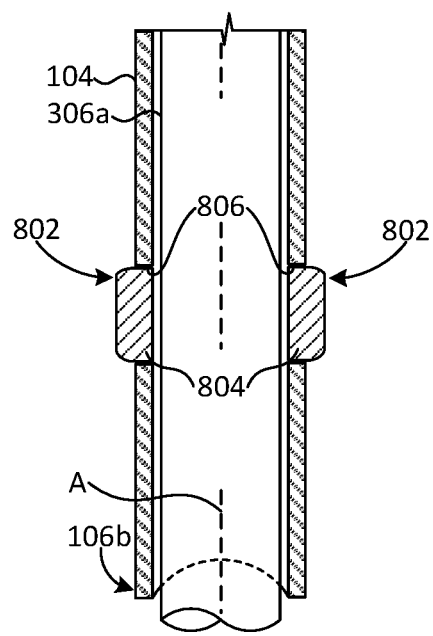

FIGS. 8B and 8C are cross-sectional side views of the distal end 106*b* of the cannula 104 and show example operation of two compliant deflection devices 802, according to one or more embodiments. As illustrated, the two compliant deflection devices 802 are provided on angularly opposite sides of the cannula 104. The radial biasing members 804 may be secured within the corresponding window 806 via a variety of attachment means including, but not limited to, one or more mechanical fasteners, an adhesive, an interference fit, a shrink fit, an over mold, or any combination thereof.

The radial biasing members 804 may be movable (transitionable) between a relaxed position, as shown in FIG. 8B, and a biased position, as shown in FIG. 8C. In FIG. 8B, the second surgical tool 306*b* is extended through the cannula 104 and the radial biasing members 804 potentially engage the outer radial surface of the second surgical tool 306*b* to help center the tool and eliminate or significantly minimize unintended oscillation and/or vibration of the second surgical tool 306*b*.

FIG. 8C shows the larger-diameter first surgical tool 306*a* extended into the cannula 104, which forces the radial biasing members 804 to partially extrude out the corresponding window 806 and away from the centerline A to accommodate the larger tool. Since the radial biasing members 804 are made of a resilient material, removing the first surgical tool 306*a* from the cannula 104 allows the radial biasing members 804 to naturally return to the relaxed position. Accordingly, the radial biasing members 804 conform to the outer diameter of the first surgical tool 306*a* and thereby eliminate or significantly minimize unintended oscillation and/or vibration of the first surgical tool 306*a*.

In one or more embodiments, the radial biasing members 804 may be made of or coated with a lubricious substance or material, which reduces the drag force of any surgical tool passing therethrough.

In some embodiments, the radial biasing members 804 may form a permanent part with the cannula 104 to be reused after proper sterilization of the trocar assembly 100 (FIGS. 1-3). In other embodiments, however, the radial biasing members 804 may be disposable and intended for one-time use. New radial biasing members 804 may be installed in the corresponding window 806 from the inside or the outside of the cannula 104 after a sterilization cycle of the trocar assembly 100.

In some embodiments, instead of having a plurality of radial biasing members 804, the compliant deflection device 802 may comprise a single, annular biasing insert secured to the inner surface of the cannula 104. The annular biasing insert may be made of a pliable material designed to flex and thereby allow varying sizes of surgical tools through the cannula 104.

Figure 9:
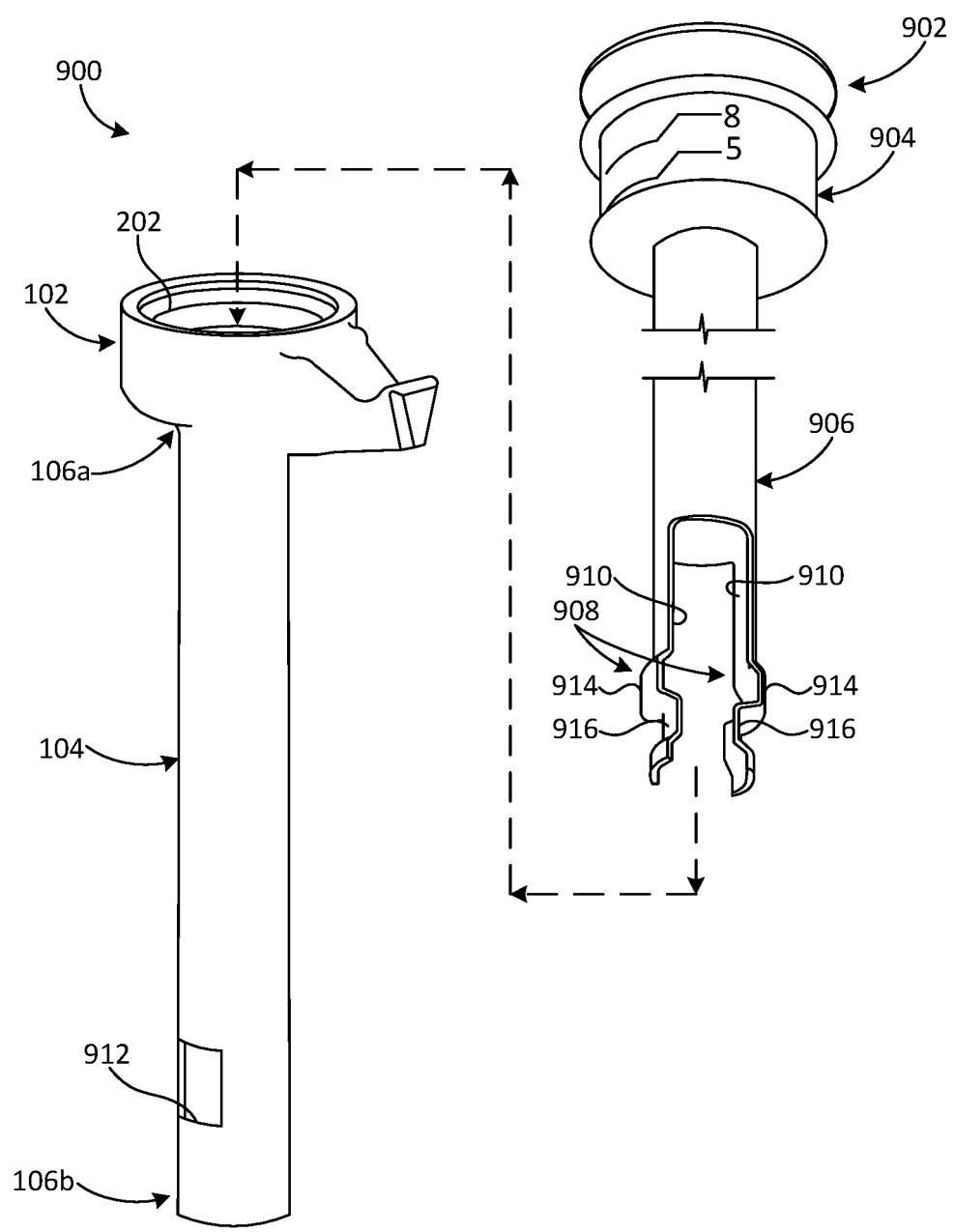
FIG. 9 is an isometric, partially exploded view of another example trocar assembly that may incorporate the principles of the present disclosure.

FIG. 9 is an isometric, partially exploded view of another example trocar assembly 900 that may incorporate the principles of the present disclosure. The trocar assembly 900 may be similar in some respects to the trocar assembly 100 of FIGS. 1-3, and therefore may be best understood with reference thereto where like numerals represent like elements not described again in detail. Similar to the trocar assembly 100 of FIGS. 1-3, the trocar assembly 900 includes the trocar housing 102 and the cannula 104 that extends distally therefrom and has the proximal and distal ends 106*a,b*. Unlike the trocar assembly 100 of FIGS. 1-3, however, the trocar assembly 900 includes a sleeve assembly 902 that is at least partially received into the housing 102 and the cannula 104.

As illustrated, the sleeve assembly 902 includes a head 904 and a sleeve 906 that extends distally from the head 904. While not shown, the head 904 may include and otherwise incorporate one or more seal assemblies, such as one or both of the seal assemblies 204*a,b* of FIGS. 2-3. When the trocar assembly 900 is assembled, the sleeve 906 extends into the cannula 104 and the head 904 is sized to be received (at least partially) into the working chamber 202.

The sleeve 906 may include one or more compliant deflection devices 908 (two shown) provided at or near the distal end of the sleeve 906. Each compliant deflection device 908 may comprise an axially extending finger separated by openings 910 defined by the sleeve 906. The openings 910 allow the compliant deflection devices 908 to flex during operation. More particularly, the sleeve 906 may be made of a resilient material that allows the compliant deflection devices 908 to provide a radially inward biasing force when acted upon by a surgical tool extended inside the sleeve 906. The sleeve 906, for example, may be made of any of the flexible or resilient materials mentioned herein. Once the surgical tool is removed from within the sleeve 906, the compliant deflection devices 908 may naturally and elastically return to a relaxed state.

While two compliant deflection devices 908 are depicted in FIG. 9, more than two compliant deflection devices 908 may be included, such as three or four. In some embodiments, the compliant deflection devices 908 may be equidistantly spaced from each other, but could alternatively be spaced in any desired configuration. Embodiments with two compliant deflection devices 908, for example, may be angularly offset from each other by approximately 180°, embodiments with three compliant deflection devices 908 may be angularly offset from each other by approximately 120°, and embodiments with four compliant deflection devices 908 may be angularly offset from each other by approximately 90°.

The compliant deflection devices 908 may be configured to interact with one or more corresponding windows 912 (one shown, one occluded) defined at or near the distal end 106*b* of the cannula 104. When the trocar assembly 900 is assembled, the compliant deflection devices 908 will be arranged at or near the distal end 106*b* of the cannula 104 to be able to interact with the windows 910. As will be appreciated, the number of windows 912 will generally be the same as the number of compliant deflection devices 908.

Each compliant deflection device 908 includes a radial protrusion 914 that extends radially outward and a radial biasing member 916 that extends radially inward. Each radial protrusion 914 may be sized to be received into a corresponding one of the windows 912 and each radial biasing member 916 may be configured to engage the outer surface of surgical tools extended within the cannula 104, which may help center the surgical tools within the cannula 104 and eliminate or significantly minimize unintended oscillation and vibration. In some embodiments, as illustrated, the radial biasing members 916 may be arcuate or "cupped" in shape to better engage the rounded outer surface of a surgical tool extended within the sleeve 906.

When the radial protrusions 914 align with and are received into the windows 912, the compliant deflection devices 908 are able to flex radially outward to accommodate larger surgical tools within the cannula 104. In contrast, when the radial protrusions 914 are misaligned with the windows 912, the radial protrusions 914 instead engage the inner wall of the cannula 104. With the radial protrusions 914 engaging the inner wall of the cannula 104, the radial biasing members 916 will be urged radially inward to accommodate smaller diameter surgical tools.

Figure 10A:
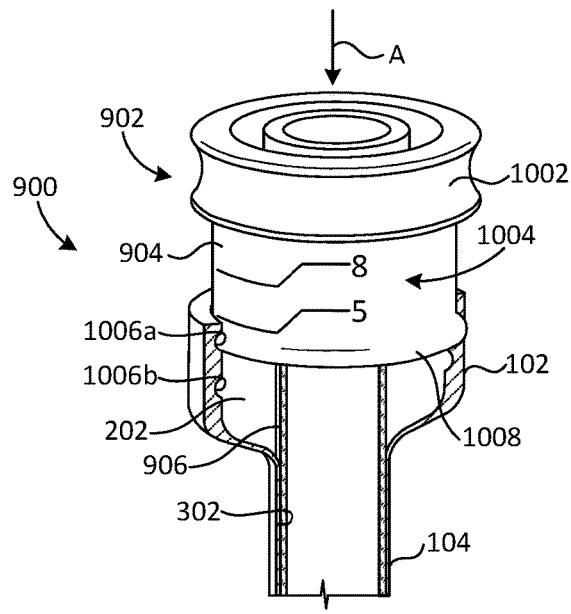
FIGS. 10A and 10B are enlarged views of the trocar assembly of FIG. 9 with the sleeve assembly in two assembled positions.
Figure 10B:
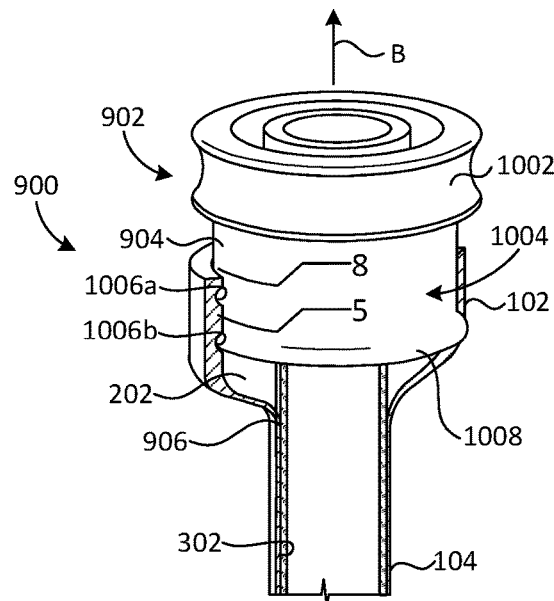

FIGS. 10A and 10B are enlarged views of the trocar assembly 900 with the sleeve assembly 902 in two assembled positions. As illustrated, when the sleeve assembly 902 is assembled in the trocar assembly 900, the head 904 is partially received into the working chamber 202 and the sleeve 906 extends distally therefrom and into the lumen 302 of the cannula 104.

In the illustrated embodiment, the sleeve assembly 902 is axially movable relative to the trocar housing 102 and the cannula 104 between a first position, as shown in FIG. 10A, and a second position, as shown in FIG. 10B. The head 904 may provide or otherwise include a grip 1002 where a user (e.g., a surgeon) is able to manually grasp the head 904 to axially move (manipulate) the sleeve assembly 902 between the first and second positions. The sleeve assembly 902, for example, is moved in a first or distal direction A to place the sleeve assembly 902 in the second position (FIG. 10B). In contrast, the sleeve assembly 902 is moved in a second or proximal direction B opposite the distal direction A to place the sleeve assembly 902 back in the first position (FIG. 10A).

In the first position, the sleeve assembly 902 may be configured to accommodate a first surgical tool (not shown) having a first outer diameter. In contrast, in the second position, the sleeve assembly 902 may be configured to accommodate a second surgical tool (not shown) having a second outer diameter that is larger than the first outer diameter. In at least one embodiment, the first surgical tool may comprise a 5 mm surgical tool, while the second surgical tool may comprise an 8 mm surgical tool. In some embodiments, as illustrated, the head 904 may include markings 1004 to indicate which size of surgical tool the sleeve assembly 902 is able to accommodate in the current position.

In some embodiments, a first groove 1006a and a second groove 1006b may be defined on the inner radial surface of the working chamber 202. The grooves 1006a,b may be axially offset from each other and generally parallel. The grooves 1006a,b may be configured to receive and mate with an annular protrusion 1008 defined on the outer radial surface of the head 904. The annular protrusion 1008 is received in the first groove 1006a when the sleeve assembly 902 is in the first position, and the annular protrusion 1008 is received in the second groove 1006b when the sleeve assembly 902 is moved to the second position. Receiving the annular protrusion 1008 into either of the grooves 1006a,b may create an interference or snap fit engagement between the trocar housing 102 and the head 904. The snap fit engagement can be overcome by grasping the head 904 at the grip 1002 and applying an axial force on the head 904 in either the distal or proximal directions A, B.

While only two grooves 1006a,b are shown in FIGS. 10A-10B, more than two grooves may be provided. In such embodiments, the sleeve assembly 902 may be configured to move to more than two positions, and thereby accommodate surgical tools of more than two sizes (diameters).

Figure 11A:
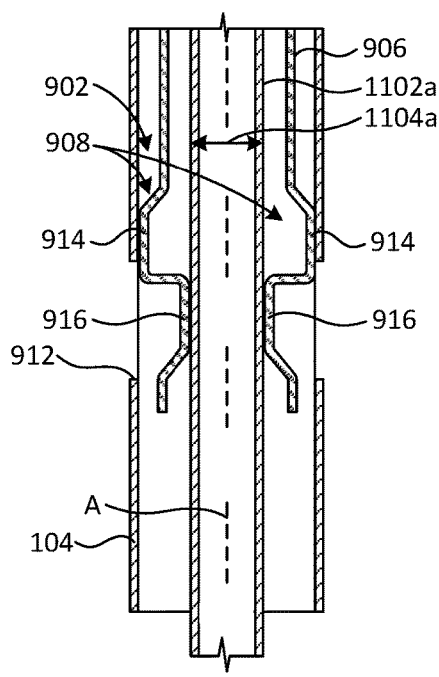
FIGS. 11A and 11B are cross-sectional side views showing the distal end of the sleeve assembly of FIG. 9 moving between the first and second positions.
Figure 11B:
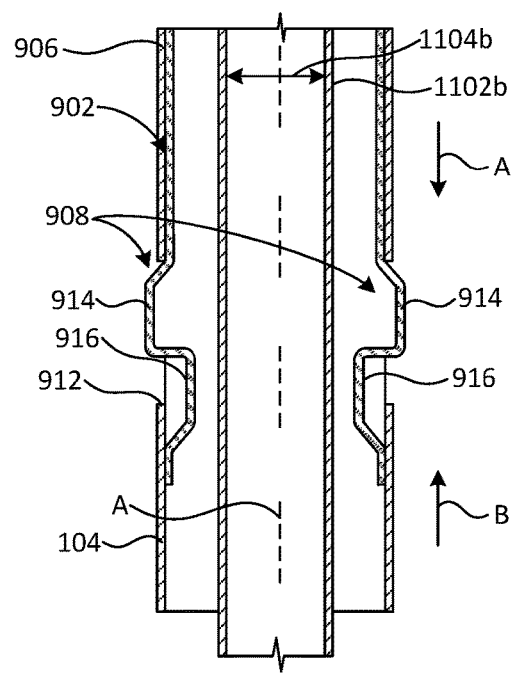

FIGS. 11A and 11B are cross-sectional side views showing the distal end of the sleeve assembly 902 moving between the first and second positions, according to one or more embodiments. More particularly, FIG. 11A shows the distal end of the sleeve assembly 902 in the first position and FIG. 11B shows the distal end of the sleeve assembly 904 having moved axially within the cannula 104 to the second position.

In the first position, the compliant deflection devices 908 are misaligned with the windows 912 such that the radial protrusions 914 engage the inner wall of the cannula 104. With the radial protrusions 914 engaging the inner wall of the cannula 104, the radial biasing members 916 are urged radially inward and toward the centerline A of the cannula 104. This allows the radial biasing members 916 to engage or come into close contact with a first surgical tool 1102a having a first outer diameter 1104a and extended within the cannula 104 (and the sleeve 906). In some embodiments, the first outer diameter may be about 5 mm and the first surgical tool 1102a may therefore be characterized as a "5 mm surgical tool." The radial biasing members 916 operate to generally center the first surgical tool 1102a within the cannula 104, and thereby eliminate or significantly minimize unintended oscillation and/or vibration of the first surgical tool 1102a.

In the second position, as shown in FIG. 11B, the sleeve assembly 902 has been moved axially in the distal direction A until the radial protrusions 914 locate, align with, and are received by the windows 912. With the radial protrusions 914 received within the windows 912, the sleeve assembly 902 is able to accommodate a second surgical tool 1102b having a second outer diameter 1104b that is larger than the first outer diameter 1104a (FIG. 11A). More specifically, as the radial protrusions 914 move into the windows 912, the radial biasing members 916 are able to expand radially outward to conform to the outer surface of the second surgical tool 1102b and thereby eliminate or significantly minimize unintended oscillation and/or vibration of the second surgical tool 1102b.

Since the compliant deflection devices 908 are made of a resilient (flexible) material, once the second surgical tool 1102b is removed from the cannula 104, the radial biasing members 916 may naturally return to their relaxed position. Moreover, in at least one embodiment, the radial biasing members 916 may be made of or coated with a lubricious substance or material, which reduces the drag force of any surgical tool (e.g., the second surgical tool 1102b) passing therethrough.

The sleeve assembly 902 can be moved back to the first position by moving the sleeve assembly 902 in the proximal direction B. Chamfered or angled surfaces provided on the radial protrusions 914 allows the radial protrusions to flex radially inward and out of the windows 912 upon being moved in the proximal direction B. Moreover, it should be noted that when surgical tools having an outer diameter larger than the second outer diameter are introduced into the trocar assembly 900, the sleeve assembly 902 may be removed and the larger-diameter surgical tools may be centered within the cannula 104 by the inner walls of the cannula 104 itself.

Figure 12:
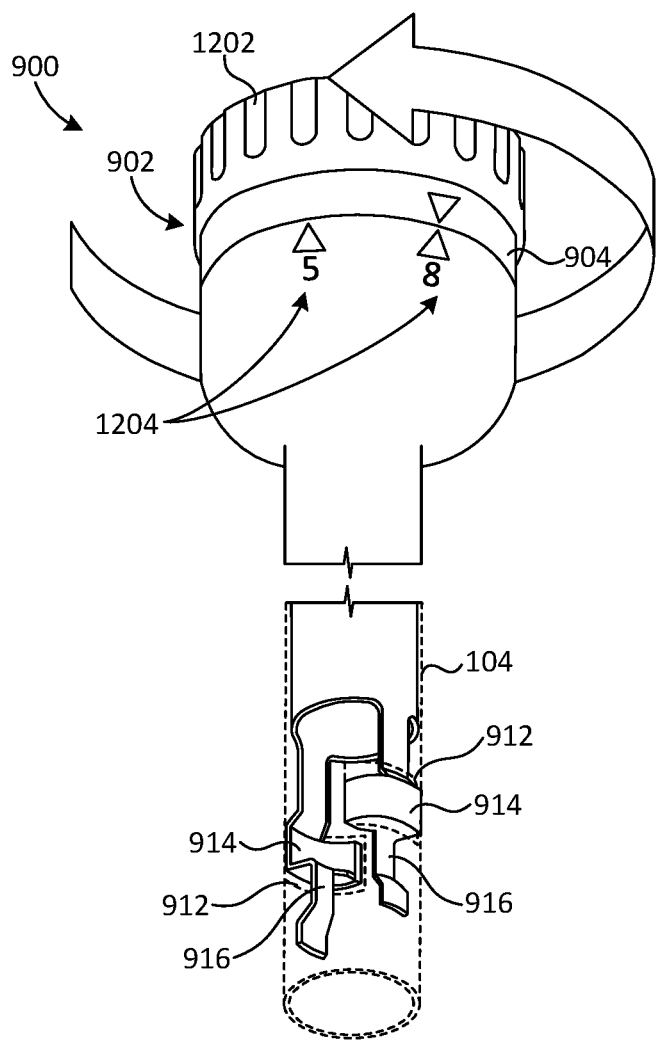
FIG. 12 is an isometric view of another embodiment of the trocar assembly of FIG. 9.

FIG. 12 is an isometric view of another embodiment of the trocar assembly 900, according to one or more additional embodiments. The illustrated embodiment may be similar in several respects to the prior embodiment shown in FIGS. 9, 10A-10B, and 11A-11B, except that the sleeve assembly 902 is movable between the first and second positions via rotation, not axial movement. More specifically, the head 904 may provide or otherwise include a grip 1202 where a user (e.g., a surgeon) is able to manually grasp the head 904 to rotationally move (manipulate) the sleeve assembly 902 between the first and second positions. In some embodiments, as illustrated, the head 904 may include markings 1204 to indicate which size of surgical tool the sleeve assembly 902 is able to accommodate in the current rotational position.

In the illustrated configuration, the sleeve assembly 902 is shown in the second position, where the radial protrusions 914 are received within the windows 912. As discussed above, the sleeve assembly 902 in the second position is able to accommodate the larger-diameter second surgical tool 1102b (FIG. 11B) as the radial biasing members 916 are able to expand radially outward to conform to the outer surface of the second surgical tool 1102b.

The sleeve assembly 902 may be moved to the first position by grasping the head 904 at the grip 1202 and rotating the head 904 as shown by the arrow. As the sleeve assembly 902 rotates, the radial protrusions 914 will move out of angular alignment with the windows 912 and engage the inner wall of the cannula 104. The curved or chamfered outer surfaces of the radial protrusions 914 may help the radial protrusions 914 move out of the windows 912. With the radial protrusions 914 engaging the inner wall of the cannula 104, the radial biasing members 916 will be correspondingly urged radially inward in preparation to receive the smaller-diameter first surgical tool 1102a (FIG. 11A).

The sleeve assembly 902 can be moved back to the second position by rotating the head 904 in the opposite direction. In either position, the radial biasing members 916 operate to center the first and second surgical tools 1102a,b within the cannula 104, and thereby eliminate or significantly minimize unintended oscillation and/or vibration of the surgical tools 1102a,b.

Embodiments disclosed herein include:

A. A trocar assembly that includes a trocar housing that defines a working chamber, a cannula having a proximal end and a distal end and defining a lumen that extends between the proximal and distal ends, wherein the cannula is coupled to the trocar housing at the proximal end to facilitate communication between the lumen and the working chamber, and a plurality of compliant deflection devices provided at or near the distal end of the cannula, wherein each compliant deflection device includes a radial biasing member that extends radially inward toward a centerline of the cannula to center a surgical tool within the lumen and minimize unintended oscillation and vibration of the surgical tool.

B. A method of using a trocar assembly that includes introducing a surgical tool into a working chamber defined by a trocar housing that communicates with a lumen defined by a cannula coupled to the trocar housing, wherein a plurality of compliant deflection devices are provided at or near a distal end of the cannula and each compliant deflection device includes a radial biasing member that extends radially inward toward a centerline of the cannula, extending the surgical tool into the lumen, and engaging an outer surface of the surgical tool with the radial biasing member of each compliant deflection device and thereby centering the surgical tool within the lumen and minimizing unintended oscillation and vibration of the surgical tool.

Each of embodiments A and B may have one or more of the following additional elements in any combination: Element 1: wherein the radial biasing member of each compliant deflection device is made of a resilient material selected from the group consisting of stainless steel, spring steel, plastic, nylon, vinyl, polyurethane, polyethylene, polypropylene, rubber, silicone, and any combination thereof. Element 2: wherein the radial biasing member of each compliant deflection device is coated with a lubricious material. Element 3: wherein the radial biasing member comprises a tab defined in a wall of the cannula. Element 4: wherein the radial biasing member comprises a longitudinal extension defined in a wall of the cannula and defines a radial projection that protrudes radially inward toward the centerline. Element 5: wherein the radial biasing member comprises a bow spring arranged within a corresponding groove defined on an inner radial surface of the cannula, and wherein the bow spring extends radially inward toward the centerline. Element 6: wherein each compliant deflection device is arranged on an outer surface of the cannula and the radial biasing member of each compliant deflection device extends through a corresponding window defined through a wall of the cannula. Element 7: wherein each compliant deflection device further includes a body received within a corresponding depression defined in the outer surface of the cannula. Element 8: wherein the radial biasing member of each compliant deflection device comprises an insert seated within a corresponding window defined through a wall of the cannula. Element 9: further comprising a sleeve assembly that includes a head at least partially receivable into the trocar housing, and a sleeve extending distally from the head and extendable into the cannula, wherein each compliant deflection device is an axially extending finger that provides the radial biasing member and further provides a radial protrusion extending radially outward to interact with a corresponding window defined by the cannula at or near the distal end. Element 10: wherein the sleeve assembly is movable between a first position, where the radial protrusion of each compliant deflection device is misaligned with the corresponding window, and a second position, where the radial protrusion of each compliant deflection device is aligned with the corresponding window.

Element 11: wherein the radial biasing member of each compliant deflection device is made of a resilient material selected from the group consisting of stainless steel, spring steel, plastic, nylon, vinyl, polyurethane, polyethylene, polypropylene, rubber, silicone, and any combination thereof. Element 12: further comprising mitigating drag against the outer surface of the surgical tool with a lubricious material coated on one or more of the radial biasing members. Element 13: further comprising moving the radial biasing member of each compliant deflection device from a relaxed position to a biased position as acted upon by the surgical tool, and allowing the radial biasing member of each compliant deflection device to naturally move back to the relaxed position upon removing the surgical tool from the lumen. Element 14: wherein the radial biasing member comprises a bow spring arranged within a corresponding groove defined on an inner radial surface of the cannula, the method further comprising radially compressing the bow spring as acted upon by the surgical tool, and axially extending at least one end of the bow spring into a pocket defined in the inner radial surface of the cannula. Element 15: wherein each compliant deflection device is arranged on an outer surface of the cannula and the radial biasing member of each compliant deflection device comprises a collapsible protrusion extending through a corresponding window defined through a wall of the cannula, the method further comprising at least partially collapsing the collapsible protrusion of each compliant deflection device as acted upon by the surgical tool, and allowing the collapsible protrusion of each compliant deflection device to re-inflate upon removing the surgical tool from the lumen. Element 16: wherein the radial biasing member of each compliant deflection device comprises an insert seated within a corresponding window defined through a wall of the cannula, the method further comprising radially compressing the insert of each compliant deflection device as acted upon by the surgical tool and thereby forcing the insert of each compliant deflection device to partially extrude out the corresponding window and away from the centerline, and allowing the collapsible protrusion of each compliant deflection device to return to a relaxed position upon removing the surgical tool from the lumen. Element 17: wherein the trocar assembly further includes a sleeve assembly that includes a head at least partially receivable into the trocar housing, and a sleeve extending distally from the head and extendable into the cannula, wherein each compliant deflection device is an axially extending finger that provides the radial biasing member and further provides a radial protrusion extending radially outward to interact with a corresponding window defined by the cannula at or near the distal end, and wherein extending the surgical tool into the lumen further comprises extending the surgical tool into the sleeve. Element 18: wherein the surgical tool is a first surgical tool having a first outer diameter, the method further comprising moving the sleeve assembly to a first position, where the radial protrusion of each compliant deflection device is misaligned with the corresponding window and the radial biasing member of each compliant deflection device is urged radially inward to accommodate first surgical tool, and moving the sleeve assembly to a second position, where the radial protrusion of each compliant deflection device is aligned with and received into the corresponding window and the radial biasing member of each compliant deflection device is able to flex radially inward to accommodate a second surgical tool having a second outer diameter larger than the first outer diameter.

By way of non-limiting example, exemplary combinations applicable to A and B include: Element 6 with Element 7; Element 9 with Element 10; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The terms "proximal" and "distal" are defined herein relative to a surgeon or robotic surgical system having an interface configured to mechanically and electrically couple a surgical tool to a robotic manipulator. The term "proximal" refers to the position of an element closer to the surgeon or the robotic manipulator and the term "distal" refers to the position of an element further away from the surgeon or the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A trocar assembly, comprising:
   a trocar housing that defines a working chamber;
   a cannula having opposing proximal and distal ends and defining a lumen that extends between the proximal and distal ends, wherein the cannula is coupled to the trocar housing at the proximal end to facilitate communication between the lumen and the working chamber;
   one or more windows defined in the cannula, each window forming an aperture defined entirely through a sidewall of the cannula; and
   one or more compliant deflection devices received within and occluding the one or more windows,
   wherein each compliant deflection device includes a radial biasing member that extends radially inward toward a centerline of the cannula, and
   wherein each compliant deflection device is compliantly expandable to conform to an outer diameter of a tool inserted within the lumen.

2. The trocar assembly of claim 1, wherein the radial biasing member of each compliant deflection device is made of a resilient material selected from the group consisting of stainless steel, spring steel, plastic, nylon, vinyl, polyurethane, polyethylene, polypropylene, rubber, silicone, and any combination thereof.

3. The trocar assembly of claim 1, wherein the radial biasing member of each compliant deflection device is coated with a lubricious material.

4. The trocar assembly of claim 1, wherein each compliant deflection device is secured to the cannula at the one or more windows and extends through a corresponding one of the one or more windows.

5. The trocar assembly of claim 1, wherein a depression is defined in an outer surface of the cannula at each window and circumscribes the window, and wherein each compliant deflection device further includes a body received within the depression.

6. The trocar assembly of claim 5, wherein each radial biasing member comprises a collapsible projection extending from the body and into the window.

7. The trocar assembly of claim 5, wherein the body is received in the depression in a flush mounted configuration.

8. The trocar assembly of claim 1, wherein each radial biasing member protrudes radially inward through a corresponding one of the one or more windows and toward a centerline of the cannula.

9. A method of using a trocar assembly, comprising:
introducing a surgical tool into a working chamber defined by a trocar housing that communicates with a cannula extending from the trocar housing, wherein one or more windows are defined in the cannula at or near a distal end of the cannula, each window forming an aperture defined entirely through a sidewall of the cannula, and one or more compliant deflection devices are received within and occluding the one or more windows;
extending the surgical tool into a lumen defined by the cannula;
engaging an outer surface of the surgical tool against a radial biasing member of each compliant deflection device, wherein the radial biasing member extends radially inward toward a centerline of the cannula; and
centering the surgical tool within the lumen with the radial biasing member and thereby minimizing unintended oscillation and vibration of the surgical tool.

10. The method of claim 9, wherein the radial biasing member of each compliant deflection device is made of a resilient material selected from the group consisting of stainless steel, spring steel, plastic, nylon, vinyl, polyurethane, polyethylene, polypropylene, rubber, silicone, and any combination thereof.

11. The method of claim 9, further comprising mitigating drag against the outer surface of the surgical tool with a lubricious material coated on the radial biasing member.

12. The method of claim 9, further comprising:
moving the radial biasing member of each compliant deflection device from a relaxed position to a biased position as acted upon by the surgical tool; and
allowing the radial biasing member of each compliant deflection device to naturally move back to the relaxed position upon removing the surgical tool from the lumen.

13. The method of claim 9, wherein each compliant deflection device is arranged on an outer surface of the cannula and the radial biasing member of each compliant deflection device comprises a collapsible protrusion extending through a corresponding one of the one or more windows, the method further comprising:
at least partially collapsing the collapsible protrusion of each compliant deflection device as acted upon by the surgical tool; and
allowing the collapsible protrusion of each compliant deflection device to re-inflate upon removing the surgical tool from the lumen.

* * * * *